(12) United States Patent
Moritomo

(10) Patent No.: US 11,490,787 B2
(45) Date of Patent: Nov. 8, 2022

(54) LEAK TESTER

(71) Applicant: HOYA CORPORATION, Tokyo (JP)

(72) Inventor: Ichiro Moritomo, Kanagawa (JP)

(73) Assignee: HOYA CORPORATION, Tokyo (JP)

( * ) Notice: Subject to any disclaimer, the term of this patent is extended or adjusted under 35 U.S.C. 154(b) by 334 days.

(21) Appl. No.: 16/854,490

(22) Filed: Apr. 21, 2020

(65) Prior Publication Data

US 2020/0337527 A1 Oct. 29, 2020

(30) Foreign Application Priority Data

Apr. 24, 2019 (JP) .............................. JP2019-083165

(51) Int. Cl.
| A61B 1/015 | (2006.01) |
| A61B 1/12 | (2006.01) |
| G01M 3/28 | (2006.01) |
| A61B 1/00 | (2006.01) |
| G01M 3/26 | (2006.01) |
| G02B 23/24 | (2006.01) |

(52) U.S. Cl.
CPC ...... *A61B 1/00057* (2013.01); *A61B 1/00119* (2013.01); *A61B 1/015* (2013.01); *A61B 1/125* (2013.01); *G01M 3/26* (2013.01); *G02B 23/24* (2013.01); *G01M 3/2815* (2013.01)

(58) Field of Classification Search
None
See application file for complete search history.

(56) References Cited

U.S. PATENT DOCUMENTS

| 7,740,813 B2 * | 6/2010 | Williams ............... A61B 1/125 422/292 |
| 7,918,788 B2 * | 4/2011 | Lin ....................... A61B 90/70 600/156 |
| 2001/0032494 A1 * | 10/2001 | Greszler ................ A61B 1/125 73/40 |

(Continued)

FOREIGN PATENT DOCUMENTS

| EP | 3431196 A1 | 1/2019 | |
| JP | 3820168 B2 * | 9/2006 | ......... A61B 1/00057 |

(Continued)

OTHER PUBLICATIONS

Extended European Search Report (EESR) dated Sep. 14, 2020 for the corresponding European Patent Application No. 20171005.0.

*Primary Examiner* — John P Leubecker
(74) *Attorney, Agent, or Firm* — Greenblum & Bernstein, P.L.C.

(57) ABSTRACT

A leak tester of the present disclosure includes: an air pump for supplying air into the endoscope device; a pressure sensor that detects a pressure inside the endoscope device, and a control unit that controls operation of the air pump and the pressure sensor. The control unit executes: a first process of judging whether an internal pressure of the endoscope device has dropped by a first pressure value within a first time span after start of a wet test; a second process of judging whether the internal pressure has further dropped by a second pressure value different from the first pressure value within a second time span different from the first time span in a case where the internal pressure has dropped by the first pressure value in the first process; and a process of judging pass or fail in the wet test.

5 Claims, 3 Drawing Sheets

(56) References Cited

U.S. PATENT DOCUMENTS

| | | | |
|---|---|---|---|
| 2006/0196250 A1* | 9/2006 | Gocho | A61B 1/00057 600/101 |
| 2007/0238923 A1* | 10/2007 | Kubach | G01M 3/26 600/118 |
| 2016/0095508 A1 | 4/2016 | Terliuc et al. | |
| 2017/0027420 A1* | 2/2017 | Choi | G01M 3/26 |
| 2019/0282078 A1 | 9/2019 | Terliuc et al. | |
| 2020/0170495 A1* | 6/2020 | Andrade | A61B 1/123 |

FOREIGN PATENT DOCUMENTS

| | | |
|---|---|---|
| JP | 2006-304906 A | 11/2006 |
| JP | 2009-142490 A | 7/2009 |
| JP | 2011-5090 A | 1/2011 |
| JP | 2016-30174 A | 3/2016 |

\* cited by examiner

LEAK TESTER

CROSS-REFERENCE TO RELATED APPLICATION

This application claims priority from Japanese Patent Application No. 2019-083165 filed with the Japan Patent Office on Apr. 24, 2019, the entire content of which is hereby incorporated by reference.

BACKGROUND

Technical Field

The present disclosure relates to a leak tester that detects an air leak in an endoscope device (scope), for example.

Related Art

For example, an occurrence of a crack (for example, due to aging, or the like) in an endoscope device (scope) can cause a water leak or an air leak during use (procedure), leading to the possibility of entrance of bacteria through the leak (crack) and its adhesion to the inside of the endoscope device. Therefore, the endoscope device must ensure airtightness.

In order to confirm whether the airtightness of the endoscope device is ensured, an inspection using a leak tester is typically performed before the procedure. With the leak tester connected to an air supply port (test air supply port) of an endoscope device, air is supplied to set the pressure inside the endoscope device to a predetermined value, and the internal pressure is monitored using a pressure sensor, thereby inspecting whether an air leak (that is, water leak) has occurred. Air leak inspection involves two types of inspection states: a dry test and a wet test. The dry test is an inspection performed in the atmosphere, and the wet test is an inspection performed in the water.
Patent Literature 1: JP 2006-304906 A

SUMMARY

In a case where a dry test is performed, the endoscope device and the leak tester are in the same environment (including all of temperature, pressure, and humidity). This enables acquisition of an appropriate inspection result. In contrast, in a case where a wet test is performed, extremely low water temperature would decrease the pressure inside the endoscope device in some cases even though no air leak has occurred in the endoscope device. The internal pressure can drop by a few kPa just because of low water temperature. This might lead to an occurrence of a phenomenon in which the internal pressure of the endoscope device would not rise at all even with attempts to raise the internal pressure. Such a phenomenon can easily occur even in hospitals, and it is necessary to appropriately detect the presence or absence of an air leak even when a wet test in low-temperature water has to be performed.

The present disclosure has been made in view of such a situation and aims to provide a leak tester capable of appropriately performing a wet test even with low water temperatures (that would not make a judgment of an air leak (error) just because of low water temperature).

In order to solve the above problems, the present embodiment provides a leak tester for inspecting the presence or absence of an air leak in an endoscope device, the leak tester including:

an air pump for supplying air into the endoscope device;
a pressure sensor that detects a pressure inside the endoscope device; and
a control unit that controls operation of the air pump and the pressure sensor and judges the presence or absence of an air leak from the endoscope device, in which the control unit executes:
a first process of judging whether an internal pressure of the endoscope device has dropped by a first pressure value within a first time span after start of a wet test;
a second process of judging whether the internal pressure has further dropped by a second pressure value different from the first pressure value within a second time span different from the first time span in a case where the internal pressure has dropped by the first pressure value in the first process; and
a process of judging pass or fail in the wet test on the basis of a result of the second process.

Further features related to the present disclosure will become apparent from the description of the present specification and the accompanying drawings. The present disclosure is achieved and implemented by elements and combinations of various elements and by modes of the following detailed description and the appended claims.

It is to be understood that the description in this specification is merely exemplary and is not intended to limit the scope of the claims or the application in any way.

According to the leak tester of the present disclosure, a wet test can be appropriately performed even in low water temperature. That is, it is possible to implement a leak tester that would not make a judgment of an air leak (error) just because of low water temperature low at the time of the wet test.

DETAILED DESCRIPTION

Hereinafter, embodiments of the present disclosure will be described with reference to the drawings. In the following, an endoscope system will be described as an exemplary embodiment of the present disclosure.

<Connection Between Leak Tester and Endoscope Device>

Figure 1:
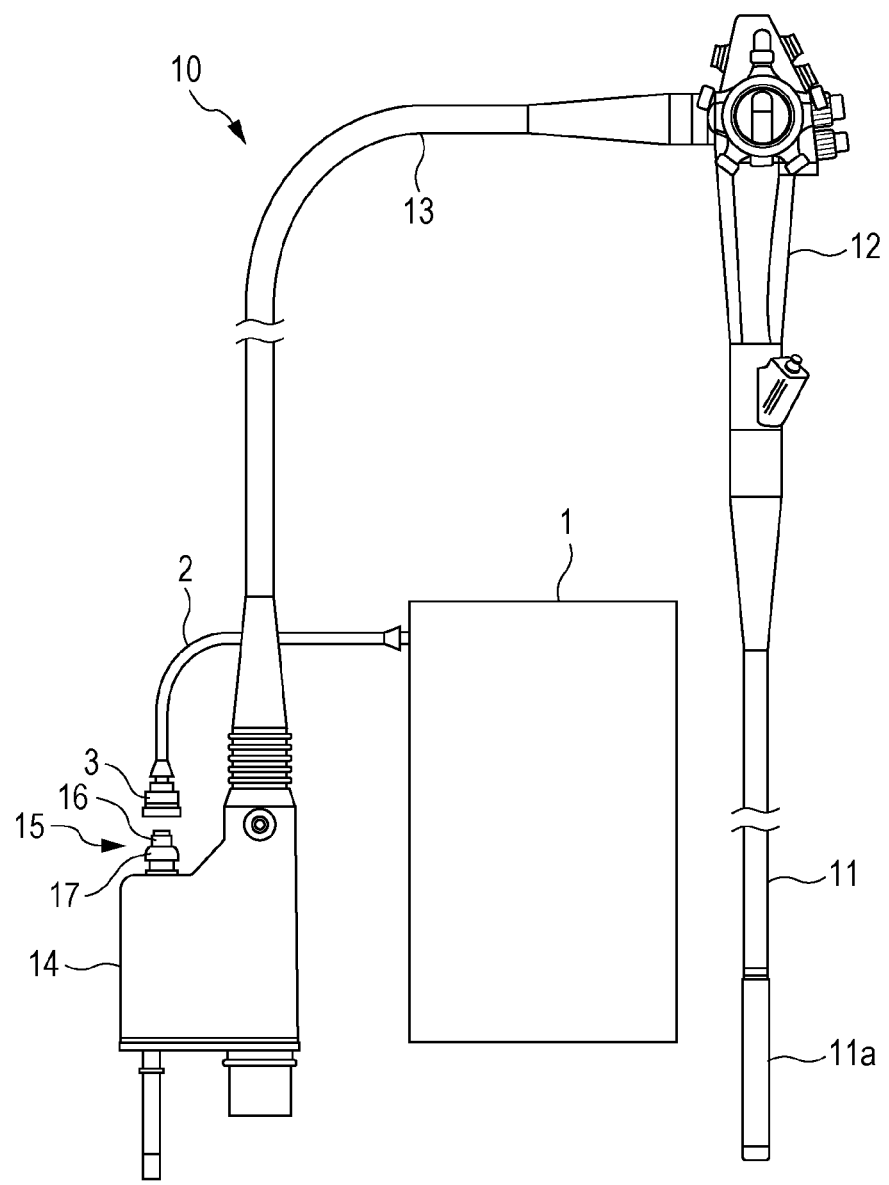
FIG. 1 is a view illustrating a use mode of a leak tester (leak inspection device) according to the present embodiment, illustrating a state where the leak tester is connected to an endoscope device.

FIG. 1 is a view illustrating a use mode of a leak tester (leak inspection device) according to the present embodiment, illustrating a state where the leak tester is connected to an endoscope device.

In FIG. 1, reference numeral 10 denotes an endoscope device, which includes a bending section 11a to be bent by remote control provided near a distal end of the flexible insertion portion 11, and which includes a connector unit 14 to be connected to a video processor (not illustrated), provided at a distal end of a joint flexible tube 13 extending rearward from an operation unit 12 joined to a proximal end of the flexible insertion portion 11.

The endoscope device 10 configured as described above is entirely connected internally in a continuous manner, and is completely airtightly shut from the outside by a partition so as to suppress entry of water or air from the outside to the inside of the endoscope device 10. The connector unit 14 includes a ventilation cap 15 for communication between the inside and the outside of the endoscope device 10.

The ventilation cap 15 can be implemented by a known product. Inside the ventilation cap 15, a movable plug 16 that closes between the outside and the inside is disposed to be biased from inside to outside by a coil spring 17. Pressing the movable plug 16 to be retracted inward against the biasing force of the coil spring 17 would allow communication between the inside and the outside of the endoscope device 10.

In the leak tester (leak inspection device) 1, connecting a connection cap 3 attached to a distal end of a communication tube 2 extending from the leak tester 1 to the ventilation cap 15 would cause the movable plug 16 to be retracted inward so as to allow the communication tube 2 to communicate with the inside of the endoscope device 10. Moreover, removing the connection cap 3 from the ventilation cap 15 in the leak tester 1 will close the ventilation cap 15 again. Thereafter, air is supplied into the endoscope device 10 by an air pump 104 provided inside the leak tester 1, and the internal pressure change over time is monitored while increasing the internal pressure, thereby detecting whether an air leak due to a crack has occurred in the endoscope device 10.

<Configuration Example of Leak Tester Including Internal Circuits>

Figure 2:
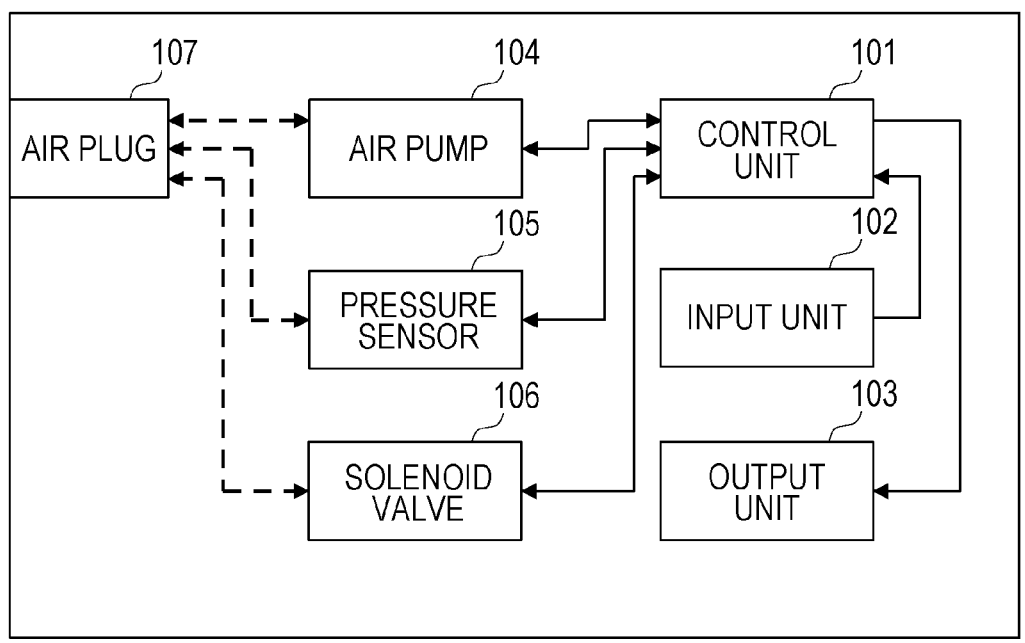
FIG. 2 is a diagram illustrating a schematic internal configuration example of a leak tester according to the present embodiment.

FIG. 2 is a diagram illustrating an internal configuration example of the leak tester 1 according to the present embodiment. In FIG. 2, a solid line indicates a control signal line, and a dotted line indicates an air passage line.

The leak tester 1 includes a control unit 101, an input unit 102, an output unit 103, an air pump 104, a pressure sensor 105, a solenoid valve 106, and an air plug 107.

The control unit 101 includes a processor such as a microprocessor or central processing unit (CPU), for example, and controls overall operation of the leak tester 1, including control of a power supply circuit (not illustrated) and the air pump 104, reading of output of the pressure sensor 105, and display control.

The input unit 102 includes a push switch, for example, and is used by an operator to input leak test type information (dry test and wet test) and input an instruction to start the leak test. An instruction signal input by the input unit 102 is provided to the control unit 101. The control unit 101 controls operation of the air pump 104, the pressure sensor 105, or the like, in response to the instruction signal.

The output unit 103 includes an LCD, an LED, and a buzzer, for example, and performs operation such as displaying a pressure target value, a current pressure value, elapsed time, and errors on the LCD, lighting or flashing a blue or red LED at leak discrimination or error occurrence, or sounding a buzzer at the time of operation switching, measurement completion (discrimination), error occurrence, or the like.

The air pump 104 has a function of supplying air into the endoscope device 10 to increase the pressure inside the endoscope device 10 (pressurizing function).

The pressure sensor 105 is implemented as a semiconductor piezo-type pressure sensor and has a function of detecting the pressure inside the endoscope device 10.

The solenoid valve 106 has a function of maintaining the air pressure inside the endoscope device 10 or exhausting the air.

The air plug 107 is connected, at one attachment port, with an air pump 104, a pressure sensor 105, and a solenoid valve 106 and can be connected, at the other attachment port, with the communication tube 2. Air is supplied from the air pump 104 to the inside of the endoscope device 10 via the air plug 107 and the communication tube 2 so as to be able to increase the pressure inside the endoscope device 10.

<Operation of Leak Tester>

Figure 3:
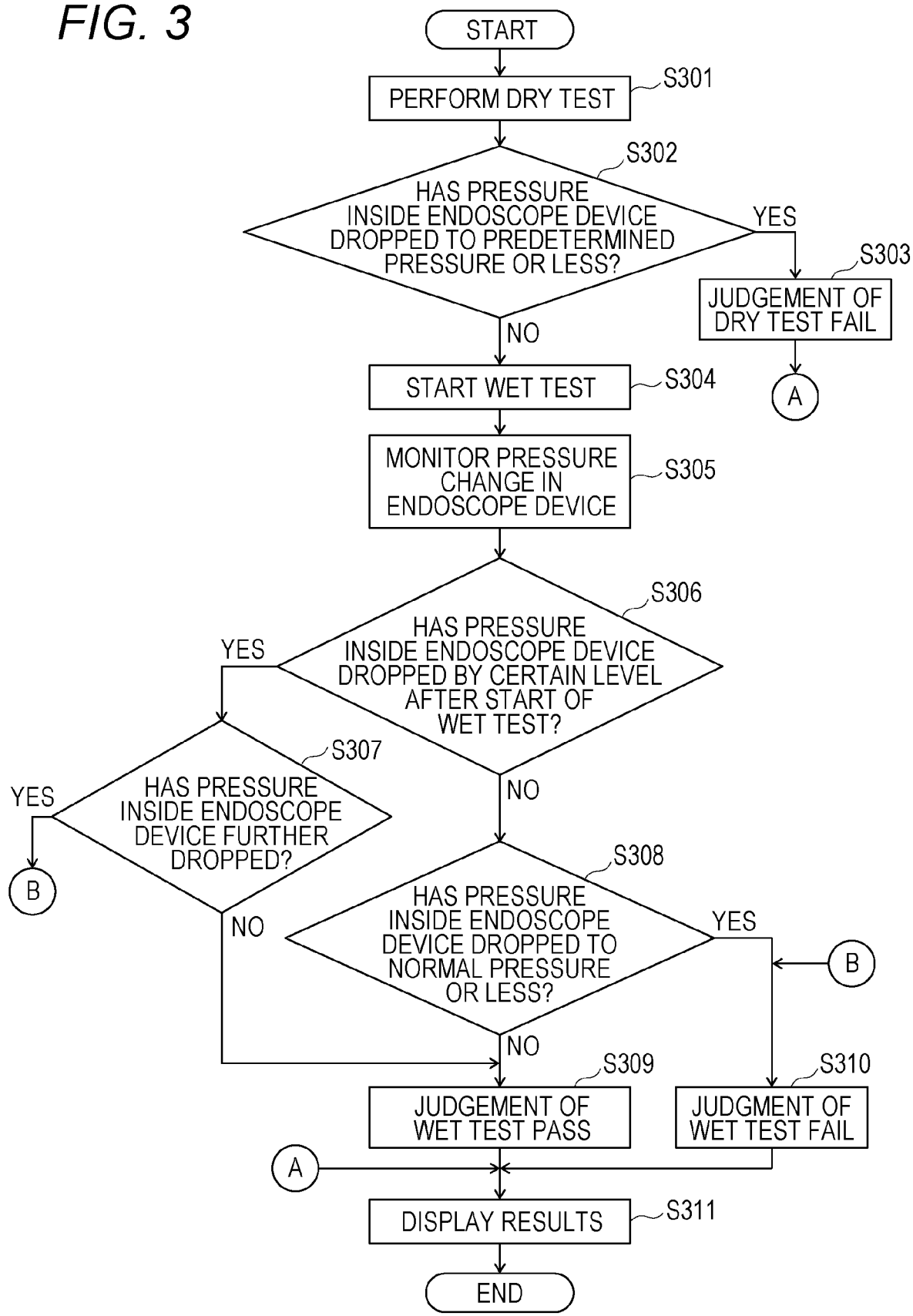
FIG. 3 is a flowchart example illustrating operation of a leak tester according to the present embodiment.

FIG. 3 is a flowchart example illustrating operation of a leak tester according to the present embodiment.

(i) Step 301

An operator connects the communication tube 2 of the leak tester 1 to the endoscope device 10 and instructs the start of a dry test using the input unit 102 of the leak tester 1. In response to this, an instruction signal (signal instructing the start of the dry test) is transmitted to control unit 101. After receiving the instruction signal, the control unit 101 operates the air pump 104 to supply air into the endoscope device 10 through the air plug 107 and the communication tube 2 so as to increase the pressure inside the endoscope device 10 to a predetermined value (20 kPa, for example). The control unit 101 monitors the internal pressure of the endoscope device 10 using the pressure sensor 105, and stops the air supply from the air pump 104 when the pressure reaches 20 kPa.

(ii) Step 302

The control unit 101 monitors a pressure value inside the endoscope device 10 detected by the pressure sensor 105 and determines whether the pressure has dropped by a predetermined value (for example, 0.8 kPa) within a predetermined time (for example, one minute). That is, it is judged whether the internal pressure of the endoscope device 10 has dropped from 20 kPa to 19.2 kPa or less within a predetermined time. In a case where a pressure drop of 0.8 kPa or more is detected (YES in step 302), the process proceeds to step 303. In a case where the pressure drop of 0.8 kPa or more is not detected (NO in step 302), the process proceeds to step 304.

(iii) Step 303

The control unit 101 makes a judgment of dry test fail and displays the inspection result on the output unit (LCD, for example) 103 (step 311).

(iv) Step 304

The control unit 101 makes a judgment of dry test pass and displays an instruction for the operator to prepare for the wet test on the output unit (LCD, for example) 103. Subsequently, the operator immerses the endoscope device 10 in the water stored in a water tank and inputs an instruction to start the wet test using the input unit 102. After receiving a wet test start instruction signal, the control unit 101 operates the air pump 104 to supply air into the endoscope device 10 through the air plug 107 and the communication tube 2 again so as to increase the pressure inside the endoscope device 10 to a predetermined value (20 kPa, for example). Note that when the internal pressure of the endoscope device 10 remains at 20 kPa at the end of the dry test, the repetitive air supply operation by the air pump 104 may be omitted.

(v) Step 305

The control unit 101 monitors a temporal change of the pressure value detected by the pressure sensor 105.

(vi) Step 306

Step 306 is a process of judging the possibility of the influence of the temperature of the water contained in the water tank. The process such as in step 306 will be performed in the present embodiment because the present inventors have found that the internal pressure of the endoscope device 10 can drop in low water temperature.

In step 306, the control unit 101 continues to monitor the pressure value inside the endoscope device 10 detected by the pressure sensor 105 and determines whether the pressure has dropped by a predetermined value (1.0 kPa, for example) immediately after the start of the wet test (within 10 seconds, for example). In a case where a pressure drop of 1.0 kPa or more is detected (YES in step 306), the process proceeds to step 307. That is, it is judged at this time that the pressure drop could have been detected due to the influence of the low water temperature, and further judgment will be made in step 307 whether the pressure has further dropped. In a case where the pressure drop of 1.0 kPa or more is not detected (NO in step 306), the process proceeds to step 308.

(vii) Step 307

In step 307, it is judged whether there is a pressure drop factor other than the water temperature. Note that the operator may check the presence or absence of an air leak visually by bending or folding the joint flexible tube 13 of the endoscope device 10 in the water tank during execution of the process of step 307.

The control unit 101 judges whether the internal pressure of the endoscope device 10 has further dropped (drop by 0.8 kPa, for example) within a predetermined time (30 seconds, for example). In a case where the pressure has further dropped (YES in step 307), the process proceeds to step 310. In a case where the pressure has not further dropped (NO in step 307), the process proceeds to step 309.

(viii) Step 308

The control unit 101 judges whether the internal pressure of the endoscope device 10 has dropped to a normal pressure (for example, 19.2 kPa) or less after a predetermined time (for example, one minute) has elapsed. That is, it is judged whether the internal pressure drop of the endoscope device 10 has reached 0.8 kPa within a predetermined time (one minute, for example). In a case where the internal pressure of the endoscope device 10 has not dropped to the normal pressure (for example, 19.2 kPa) or less (NO in step 308), the process proceeds to step 309. In a case where the internal pressure of the endoscope device 10 has dropped to the normal pressure (for example, 19.2 kPa) or less (YES in step 308), the process proceeds to step 310.

(ix) Step 309

The control unit 101 makes a judgment of wet test pass.

(x) Step 310

The control unit 101 makes a judgment of wet test fail.

(xi) Step 311

The control unit 101 displays an inspection result (pass or fail) on the output unit (for example, LCD) 103. The types of inspection results include dry test fail (wet test would not be performed in this case), dry test pass/wet test pass, or dry test pass/wet test fail.

<Specific Matters of the Present Disclosure>

(1) Specific Matter 1

A leak tester for inspecting presence or absence of an air leak in an endoscope device, the leak tester including:

an air pump for supplying air into the endoscope device;

a pressure sensor that detects a pressure inside the endoscope device; and a control unit that controls operation of the air pump and the pressure sensor and judges the presence or absence of an air leak from the endoscope device, in which the control unit executes:

a first process of judging whether an internal pressure of the endoscope device has dropped by a first pressure value within a first time span after start of a wet test;

a second process of judging whether the internal pressure has further dropped by a second pressure value different from the first pressure value within a second time span different from the first time span in a case where the internal pressure has dropped by the first pressure value in the first process; and a process of judging pass or fail in the wet test on the basis of a result of the second process.

(2) Specific Matter 2

The leak tester according to specific matter 1, in which the control unit further executes:

a third process of judging whether the internal pressure has further dropped by a third pressure value different from the first pressure value within a third time span different from the first time span, in a case where the internal pressure has not dropped by the first pressure value in the first process; and a process of judging pass or fail in the wet test on the basis of a result of the third process. Note that the second pressure value and the third pressure value may be set to a same value or different values.

(3) Specific Matter 3

The leak tester according to specific matter 2, in which the second pressure value and the third pressure value are set to a same value.

(4) Specific Matter 4

The leak tester according to any one of specific matters 1 to 3, in which the control unit performs a dry test before the wet test.

(5) Specific Matter 5

The leak tester according to specific matter 4, in which the control unit performs the wet test only when a result of the dry test is pass.

(6) Specific Matter 6

The leak tester according to specific matters 2 or 3, in which the first pressure value is set to a value greater than the second pressure value.

<Other Modes>

The functions of the present embodiment described above can also be implemented with software program codes. In this case, a storage medium recording the program code is provided to a system or a device, and then, a computer (or CPU, MPU, etc.) of the system or the device reads the program code stored in the storage medium. In this case, the program code read from the storage medium implements the functions of the above-described embodiments, and the program code and the storage medium storing the program code are configured to achieve the present disclosure. Examples of the storage medium applicable for supplying such a program code include a flexible disk, CD-ROM, DVD-ROM, hard disk, optical disk, magneto-optical disk, CD-R, magnetic tape, nonvolatile memory card, or ROM.

Moreover, it is allowable to have a configuration in which an operating system (OS) running on the computer performs part or all of actual processes on the basis of the instructions of the program code, and the functions of the above-described embodiments are implemented by the processes. Furthermore, it is also allowable to have a configuration in which the program code read from the storage medium is first written in the memory on the computer, and thereafter the computer CPU or the like performs part or all of the actual processes on the basis of the instruction of the program code, so as to implement the functions of the above-described embodiments by the processes.

Furthermore, it is also allowable to have a configuration in which the program code of the software for implementing the functions of the embodiment is distributed via a network, the program code is subsequently stored in a storage means such as a hard disk or memory of a system or device, or a storage medium such as a CD-RW or CD-R, and the computer (or CPU, MPU, etc.) of the system or device reads and executes the program code stored in the storage means or the storage medium at the time of use of the program code.

Finally, it should be understood that the processes and techniques described herein are not inherently related to any particular device, and can be implemented by any suitable combination of components. In addition, various types of general purpose devices can be used in accordance with the teaching described herein. It may prove useful to build a dedicated device to execute the steps in the method described herein. Various inventions can be formed by appropriately combining a plurality of components disclosed in the embodiments. For example, some components may be deleted from all the components illustrated in the embodiment. Furthermore, components of different embodiments may be appropriately combined with each other. Although the present disclosure has been described with reference to specific examples, these are in all respects illustrative rather than restrictive. Those skilled in the art will recognize that there are numerous combinations of hardware, software, and firmware that are suitable to implement the present disclosure. For example, the software in description can be implemented in a wide range of programs or script languages such as assembler, C/C++, perl, Shell, PHP, Java (registered trademark).

Furthermore, in the above-described embodiment, control lines and information lines are considered to be necessary for explanation, and these are not necessarily illustrating control lines and information lines associated with the product. All the components may be connected to each other.

In addition, other implementations of the present disclosure will become apparent to those skilled in the art in consideration of the specification and embodiments of the present disclosure provided herein. The various aspects and/or components of the described embodiments can be used alone or in any combination. The specification and examples are merely exemplary, and the scope and spirit of the present disclosure is set forth in the following claims.

What is claimed is:

1. A leak tester for inspecting presence or absence of an air leak in an endoscope device, comprising:
an air pump for supplying air into the endoscope device;
a pressure sensor that detects a pressure inside the endoscope device; and
a processor that controls operation of the air pump and the pressure sensor and judges the presence or absence of an air leak from the endoscope device,
wherein the processor executes:
a first process of judging whether an internal pressure of the endoscope device has dropped by a first pressure value within a first time span after start of a wet test;
a second process of judging whether the internal pressure has further dropped by a second pressure value different from the first pressure value within a second time span different from the first time span in a case where the internal pressure has dropped by the first pressure value in the first process; and
a process of judging pass or fail in the wet test on the basis of a result of the second process, and
the processor further executes:
a third process of judging whether the internal pressure has further dropped by a third pressure value different from the first pressure value within a third time span different from the first time span, in a case where the internal pressure has not dropped by the first pressure value in the first process; and
a process of judging pass or fail in the wet test on the basis of a result of the third process.

2. The leak tester according to claim 1,
wherein the second pressure value and the third pressure value are set to a same value.

3. The leak tester according to claim 1,
wherein the processor performs a dry test before the wet test.

4. The leak tester according to claim 3,
wherein the processor performs the wet test only when a result of the dry test is pass.

5. The leak tester according to claim 1,
wherein the first pressure value is set to a value greater than the second pressure value.

* * * * *